US011000057B2

(12) United States Patent
Longo et al.

(10) Patent No.: US 11,000,057 B2
(45) Date of Patent: *May 11, 2021

(54) FASTING MIMICKING AND ENHANCING DIET FOR TREATING HYPERTENSION AND LIPID DISORDERS

(71) Applicant: UNIVERSITY OF SOUTHERN CALIFORNIA, Los Angeles, CA (US)

(72) Inventors: Valter D. Longo, Playa Del Rey, CA (US); Sebastian Brandhorst, Redondo Beach, CA (US); Min Wei, West Covina, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/148,251

(22) Filed: May 6, 2016

(65) Prior Publication Data

US 2016/0324193 A1 Nov. 10, 2016

Related U.S. Application Data

(60) Provisional application No. 62/157,602, filed on May 6, 2015.

(51) Int. Cl.
*A23L 33/00* (2016.01)
*A23L 33/20* (2016.01)

(52) U.S. Cl.
CPC ............ *A23L 33/30* (2016.08); *A23L 33/20* (2016.08); *A23L 33/40* (2016.08)

(58) Field of Classification Search
CPC combination set(s) only.
See application file for complete search history.

(56) References Cited

U.S. PATENT DOCUMENTS

| 8,211,700 | B2 | 7/2012 | Longo |
| 8,728,815 | B2 | 5/2014 | Longo |
| 8,865,646 | B2 | 10/2014 | Longo |
| 9,237,761 | B2 | 1/2016 | Longo et al. |
| 9,386,790 | B2 * | 7/2016 | Longo ............ A23L 33/30 |
| 2005/0019475 | A1 | 1/2005 | Plank et al. |
| 2011/0118528 | A1 | 5/2011 | Longo et al. |
| 2012/0301559 | A1 | 11/2012 | Pridmore-Merten et al. |
| 2013/0045215 | A1 | 2/2013 | Longo et al. |
| 2013/0316948 | A1 | 11/2013 | Longo et al. |
| 2014/0112909 | A1 | 4/2014 | Longo et al. |
| 2014/0227373 | A1 | 8/2014 | Longo et al. |
| 2014/0328863 | A1 | 11/2014 | Longo |
| 2015/0004280 | A1 * | 1/2015 | Longo ............ A23L 33/40 426/2 |
| 2015/0133370 | A1 | 5/2015 | Longo |
| 2015/0250771 | A1 | 9/2015 | Longo et al. |
| 2016/0303056 | A1 * | 10/2016 | Longo ............ A61K 38/28 |
| 2016/0331016 | A1 | 11/2016 | Longo et al. |
| 2017/0000183 | A1 | 1/2017 | Longo et al. |
| 2017/0027217 | A1 | 2/2017 | Longo et al. |
| 2017/0035093 | A1 | 2/2017 | Longo et al. |
| 2017/0035094 | A1 | 2/2017 | Longo et al. |

FOREIGN PATENT DOCUMENTS

| CN | 104305206 | 1/2015 |
| RU | 2147228 C1 | 4/2000 |
| RU | 2405427 | 4/2000 |
| RU | 2528480 | 9/2014 |
| WO | 2005/032470 A2 | 4/2005 |
| WO | 2011/050302 A2 | 4/2011 |
| WO | 2012/030919 A2 | 3/2012 |
| WO | 2015/002972 A1 | 1/2015 |
| WO | 2015/134837 | 9/2015 |
| WO | 2015/153850 A2 | 10/2015 |
| WO | 2016/168802 A2 | 10/2016 |

OTHER PUBLICATIONS

Laakso et al., "Effects of Hypocaloric Diet and Insulin Therapy on Metabolic Control and Mechanisms of Hyperglycemia in Obese Non-Insulin-Dependent Diabetic Subjects", Metabolism, 1988; 1092-1100 (Year: 1988).*
Brown et al., "Intermittent fasting: a dietary intervention for prevention of diabetes and cardiovascular disease?", The British Journal of Diabetes and Vascular Disease, 2013; 68-72 (Year: 2013).*
Wilcox, "Insulin and Insulin Resistance", Clin Biochem Rev, 2005, pp. 19-39 (Year: 2005).*
U.S. Appl. No. 15/297,672, filed Oct. 19, 2016, inventors: Valter D. Longo et al.; Applicant: University of Southern California, title: "Methods and Formulations Promoting Tissue/Organ Regeneration, Longevity and Healthspan", 85 pgs.
Duarte, S.M.B. et al., "Hypocaloric high-protein diet improves clinical and biochemical markers in patients with nonalcoholic fattery liver disease (NAFLD)," Nutr. Hosp. 2014; 29(1); pp. 94-101.
Brandhorst, E. et al., "A Periodic Diet that Mimics Fasting Promotes Multi-System Regeneration, Enhanced Cognitive Performance, and Healthspan," Cell Metabolism 22, 2015, pp. 1-14.
Cheng, C. W. et al., "Fasting Mimicking Diet Promotes Ngn3-Driven β-Cell Regeneration to Reverse Diabetes," Cell 168, 2017, pp. 775-788.
Choi, I.Y. et al., "A Diet Mimicking Fasting Promotes Regeneration and Reduces Autoimmunity and Multiple Sclerosis Symptoms," Cell Reports 15, 2016, 38 pgs.

(Continued)

*Primary Examiner* — Lianko G Garyu
(74) *Attorney, Agent, or Firm* — Brooks Kushman P.C.

(57) ABSTRACT

Methods for lowering hypertension, elevated total cholesterol, elevated glucose and insulin, elevated IGF-1, elevated triglyceride levels, and/or elevated CRP levels, and elevated liver fat without negatively affecting or lowering the levels of these markers/factors in subjects with already low levels of these markers are provided. A method for elevating stem cells and regeneration and anti-inflammatory agents is also provided. Finally, a method for treating metabolic syndrome is also provided. A hypocaloric or calorie free diet or a fasting mimicking diet is administered for a first time period to the subject to reduce blood pressure or the levels of the above markers/risk factors for aging and age-related diseases.

8 Claims, 14 Drawing Sheets

(56) References Cited

OTHER PUBLICATIONS

Di Biase, S. et al., "Fasting-Mimicking Diet Reduces O-1 to Promote T Cell Mediated Tumor Toxicity," Cancer Cell 30, 2016, pp. 136-146.
Rangan, P. et al., "Fasting-Mimicking Diet Modulates Microbiota and Promotes Intestinal Regeneration to Reduce Inflammatory Bowel Disease Pathology," Cell Reports 26, 2019, pp. 2704-2719.
Wel M. et al., "Fasting-mimicking Diet and Markers/Risk Factors for Aging, Diabetes, Cancer, and Cardiovascular Disease," Sci. Transl. Med. 9, 2017, 12 pgs.
Goldhamer, A. et al., "Medically Supervised Water-only Fasting in the Treatment of Hypertension," J. of Manipulative and Physiological Therapeutics, v. 24, n. 5, 2001, pp. 335-650.
Samad, F., "Effects of Fasting on Blood Pressure in Normotensive Males," J. Fasting Health, 2016; 4(2): pp. 75-76.
Wan, R. et al., "Intermittent Food Deprivation Improves Cardiovascular and Neuroendocrine Responses to Stress in Rates," American Society for Nutritional Sciences, 2003, pp. 1921-1929.
Supplemental European Search Report dated Nov. 27, 2018 for EP Appn. No. 16790137 filed Nov. 15, 2017, 16 pgs.
Aksungar, F.B. et al., "Interleukin-6, C-reactive protein and biochemical parameters during prolonged fasting", BIOSIS, 2017, Clarivate Analys, 1 pg.
Al-Shafei, A.I., "Ramadan fasting ameliorates oxidative stress and improved glycemic control and lipid profile in diabetic patients," Eur. J. Nutr. 2014, 53, pp. 1475-1481.
Baumeier, C. et al., "Caloric restriction and intermittent fasting alter hepatic lipid droplet proteome and diacylglyercol species and prevent diabetes in NZO mice," Biochimica et Biophysica Acta 1851 (2016), pp. 566-676.
Cheng, C-W et al., "Prolonged Fasting reduces IGF-1/PKA to promote hematopoietic stem cell-based regeneration and reverse immunosuppression," Cell Stem Cell, 2014; 14(6): pp. 810-823.
Eshghinia, S. et al., "The effects of modified alternate-day fasting diet on weight loss and CAD risk factors in overweight and obese women," J. of Diabetes & Metabolic Disorders, 2013, 12:4, pp. 1-4.
Harvie, M.N. et al., "The effects of intermittent or continuous energy restriction on weight loss and metabolic disease risk markers: a randomized trial in young overweight women," Int'l J. of Obesity, 2011, 35, pp. 714-727.
Khazali, H. et al., "Effect of stress on fasting-induced ghrelin, orexin and galanin secretion in male rats fed different levels of their energy requirement," 2013, 1 pg.
Nematy, M. et al., "Effects of Ramadan fasting on cardiovascular risk factors: a prospective observational study," Nutrition Journal 2012, 11:69, pp. 1-7.
Varady, K.A. et al., "Alternate day fasting for weight loss in normal weight and overweight subjects: a randomized controlled trial," Nutrition Journal 2013, 12:146, pp. 1-8.
Wilson, J.L., "The Anti-Inflammatory Effects of Cortisol," https://adrenalfatique.org/the-anti-inflammatory-effects-of-cortisol/, 2014, 6 pgs.
Extended Search Report dated Mar. 22, 2019 for EP Appn. No. 16790137.0, 37 pgs.
Aksungar, A. et al., "Interleukin-6, C-Reactive Protein and Biochemical Parameters during Prolonged Intermittent Fasting," Ann Nutr Metabl 2007; v, 51; pp. 88-95.
Joibari, M,M. and Khazali, H., "Effects of stress on fasting-iduced ghrelin, orexin and galanin secretion in male rats fed different levels of their energy requirement," Obesity, v. 21, n. 1, Jan. 2013, pp. 130-134.
Preliminary Examination Report dated Dec. 17, 2019 for Brazilian Appn. No. 112017023748-2 filed Nov. 3, 2017, English translation, 6 pgs.
Samad, F. et al., "Effects of Ramadan Fasting on Blood Pressure in Normotensive Males," J Ayub Med Coll Abbottahad, 2015, 27(2), pp. 338-342.
Wan, R. et al., "Periodic Fasting improves Cardiovascular and Neuroendocrine Stress Adaptation," (XP-002786330), Biosis, Biosciences Information Service, Philadelphia, PA (2002), Database accession No. PREV200300282636, 1 pg.

\* cited by examiner

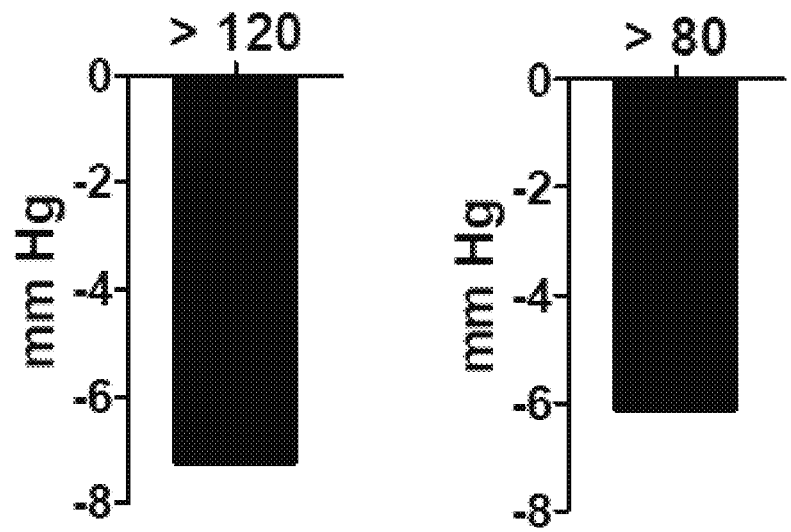
Fig. 4F
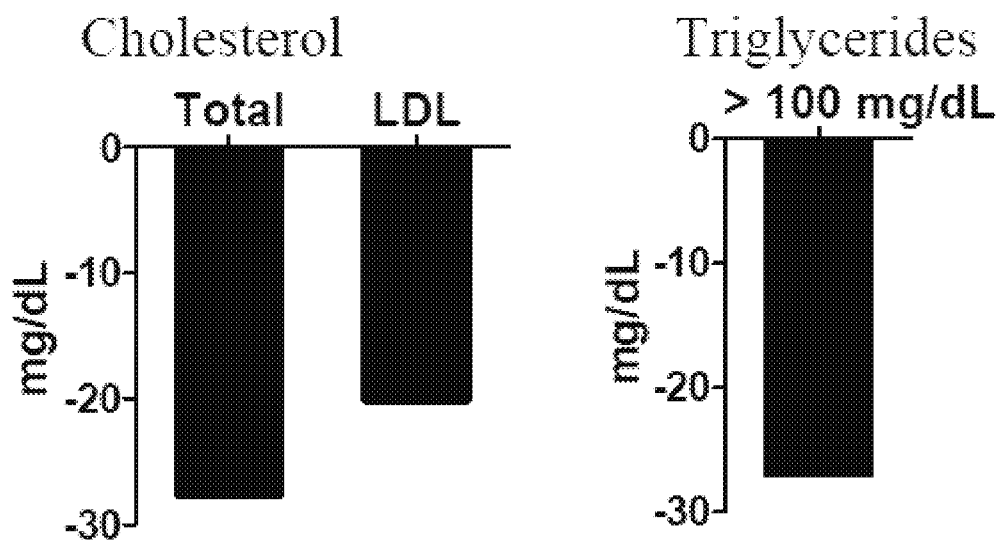
Fig. 4G
Fig. 4H

FASTING MIMICKING AND ENHANCING DIET FOR TREATING HYPERTENSION AND LIPID DISORDERS

CROSS-REFERENCE TO RELATED APPLICATIONS

This application claims the benefit of U.S. provisional application Ser. No. 62/157,602 filed May 6, 2015, the disclosure of which is hereby incorporated in its entirety by reference herein.

STATEMENT REGARDING FEDERALLY SPONSORED RESEARCH OR DEVELOPMENT

The invention was made with Government support under Contract No. AG055369 awarded by the National Institutes of Health (NIH). The Government has certian rights to the invention.

TECHNICAL FIELD

In at least one aspect, the present invention relates to methods for treating hypertension, obesity, elevated total cholesterol, elevated triglyceride levels, elevated glucose, levels, elevated insulin levels, and/or elevated CRP levels.

BACKGROUND

Growth hormone (GH)/Insulin-like Growth Factor 1 (IGF-1) signaling exerts a variety of physiological effects including promotion of growth, induction of lipolysis and gluconeogenesis, blocking lipogenesis and insulin functioning, activation of immune cells and boosting muscle mass growth. These physiological functions are mediated through binding of GH to the growth hormone receptor (GHR) on the cell surface of target cells. A key function of GH is mediated through the liver production of IGF-1. Deficiencies in GH/insulin/IGF-1 signaling extend lifespan in organisms ranging from yeast to mammals. Moreover, GHR deficiency is associated with a major reduction in pro-aging signaling, cancer, and diabetes in humans. Hypocaloric or calorie free diets or fasting mimicking diets can enhance the protection of normal tissues from toxins such as chemotherapy drugs, increase tissue regeneration, promote organism healthspan, as well as augment biomarkers associated with age-related diseases, all of which are mediated mainly via reduction of circulating IGF-1.

Dietary/calorie restriction (DR/CR) are well known in improving healthspan in model organisms and possibly in humans. However, it requires a long-term (possibly lifelong) commitment in order to reap the benefits of DR/CR, which imposes significant burden on the practitioners. Chronic DR/CR may not be feasible (hard to maintain) but also not safe for certain practitioners due to the significant weight loss. Prolonged fasting may also be difficult and potentially introduce acute malnutrition.

Accordingly, there is a need for improved dietary methods for treating certain conditions amenable to treatment by diet.

SUMMARY

Methods for treating hypertension, elevated total cholesterol, elevated triglyceride levels, and/or elevated CRP levels are provided. A hypocaloric, calorie free or fasting mimicking diet is administered for a first time period to the subject to reduce blood pressure and/or these levels of cholesterol, triglycerides, and/or CRP.

The results provided below show that adoption of periodic cycles of fasting mimicking diets (FMDs) can manage body weight, reduce inflammation, modulate risk factors associated with age-related diseases, e.g. metabolic syndrome, diabetes, cardiovascular diseases, neurodegenerative diseases (Alzheimer's disease, etc.), attenuate/delay changes in biomarkers associated with aging, reduce blood pressure, and/or reduce levels of cholesterol, triglycerides, and CRP.

BRIEF DESCRIPTION OF THE DRAWINGS

FIGS. 4A, 4B, 4C, 4D, 4E, 4F, 4G, 4H, 4I, 4J, and 4K. Generally healthy participants were subjected to 3 cycles of a fasting mimicking diet (FMD) in three months and returned to their normal diet after each cycle. The 3 cycles of the FMD reduced the body weight (A), waist circumference (B), and abdominal fat (C) in obese (BMI>30) and overweight (BMI>25) people after they had returned to their normal diet for 1 week after cycle 3. FMD reduced fasting blood sugar in people with pre-diabetes (fasting glucose >99 mg/dL). FMD reduced circulating IGF-1 levels (E). FMD reduced both systolic and diastolic blood pressure in people with above normal blood pressure (>120/80 mmHg). FMD reduced total cholesterol and LDL levels (G). FMD reduced triglycerides and CRP levels in people with relatively high levels of triglycerides (H) and CRP (I). FMD increased blood cortisol level (J) and circulating mesenchymal stem/progenitor cells (MSPC) (K).

DETAILED DESCRIPTION

Figure 1A:
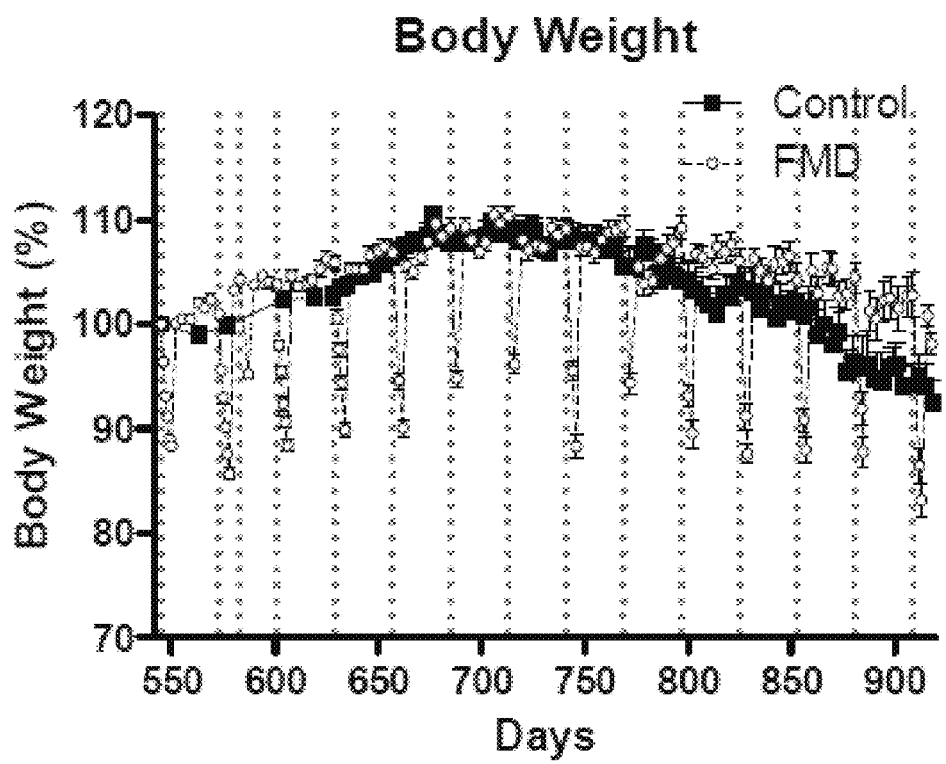
FIGS. 1A, 1B, 1C, 1D, 1E, 1F, and 1G. Starting at 17-month of age, female C57BL/6 mice were subjected to cycles of 5-day FMD every 2 weeks. A) Mice fed with FMD regained body weight upon refeeding. FMD is not associated with chronic body weight loss. B) Cycles of FMD initiated at middle age (17 month old) extended mean lifespan. FMD reduced blood glucose (C), IGF-1 (D) and insulin (E), all of which recovered after refeeding of normal diet. FMD increased white blood cell (WBC) (F) and lymphocyte (LYM) (G) counts.
Figure 1B:
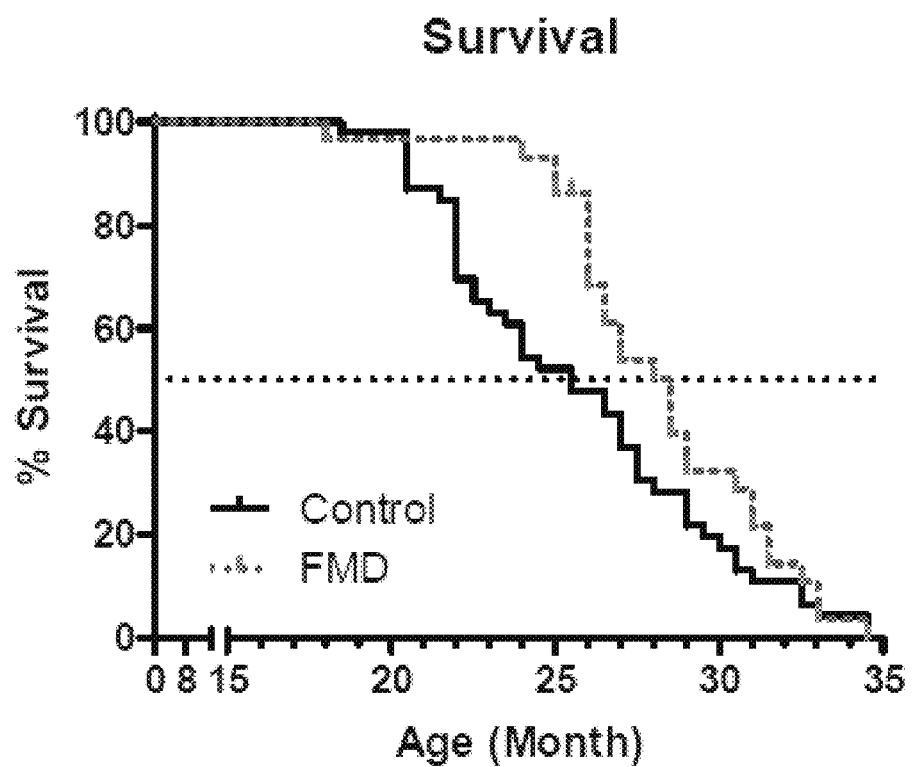
Figure 1C:
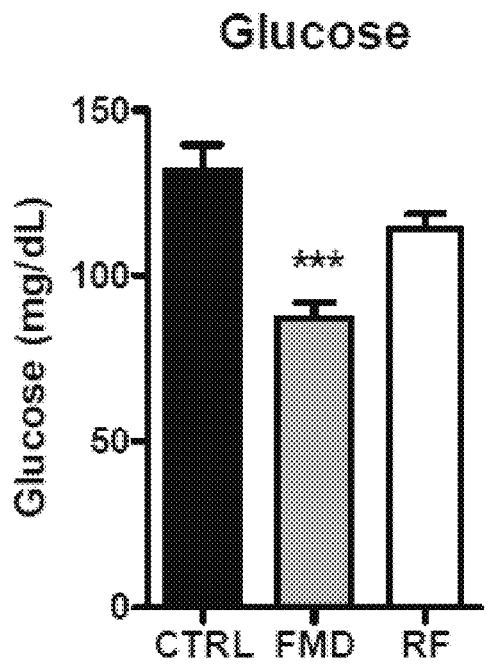
Figure 1D:
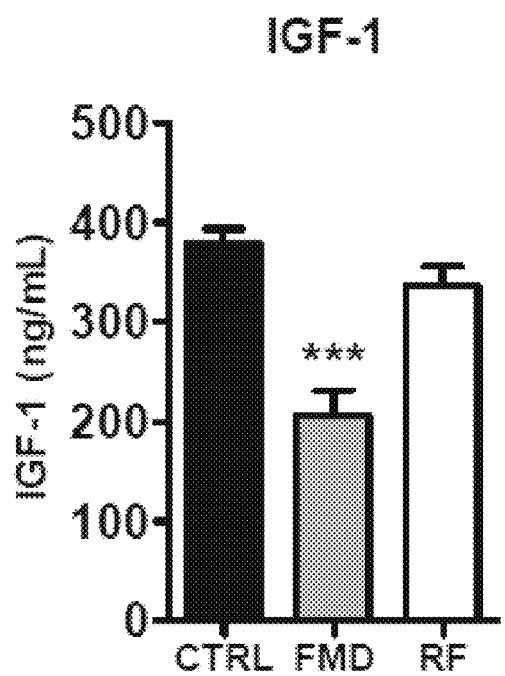
Figure 1E:
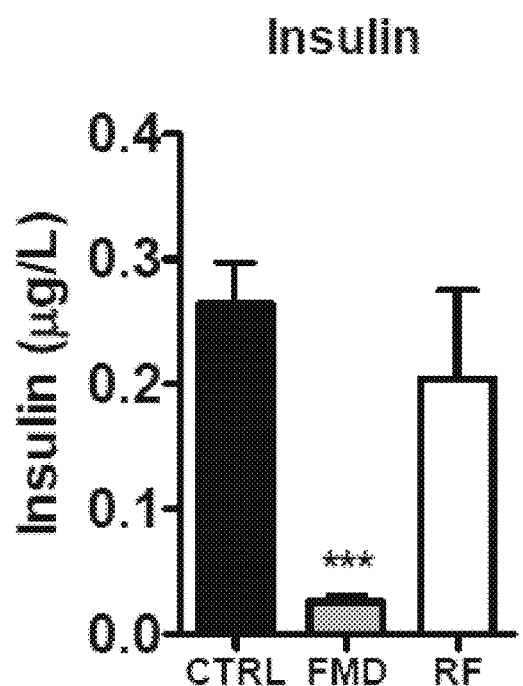
Figure 1F:
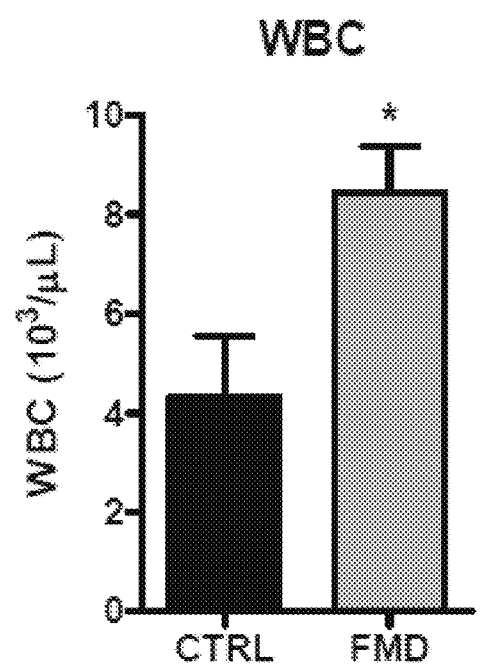
Figure 1G:
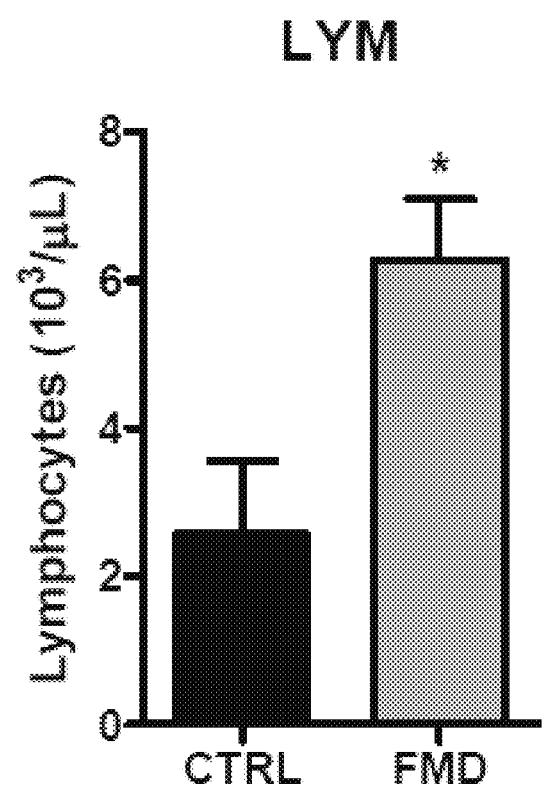

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

ABBREVIATIONS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

"AL" means ad libitum.
"BMI" means body mass index.
"CRP" means C-reactive protein.
"FMD" means fasting mimicking diet.
FMED" means fasting mimicking and enhancing diet. It is a type of FMD that also provides various supplements.
"STS" means short-term starvation.

The terms "kilocalorie" (kcal) and "Calorie" refer to the food calorie. The term "calorie" refers to the so-called small calorie.

The term "subject" refers to a human or animal, including all mammals such as primates (particularly higher primates), sheep, dog, rodents (e.g., mouse or rat), guinea pig, goat, pig, cat, rabbit, and cow.

In an embodiment, a method for treating hypertension in a subject is provided. The method includes a step of identifying a subject having hypertension. A hypocaloric or calorie free diet (e.g., STS) or a fasting mimicking diet (FMD) is administered for a first time period to the subject to reduce systolic blood pressure and/or diastolic blood pressure. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In another refinement, STS or a FMD is repeated a plurality of times at predetermined intervals. In a further refinement, the hypocaloric or calorie free diet or fasting mimicking diet is administered for a period of 5 days every 2-24 weeks or 1-2 days every week. For example, a hypocaloric or calorie free diet or a FMD can be repeated at intervals from one week to 6 months. Typically, the subject is administered a normal diet in between these repetitions.

In another embodiment, a method for treating elevated triglycerides, inflammation, and/or CRP levels in a subject is provided. The method includes a step of identifying a subject having elevated triglycerides and/or CRP or other inflammatory markers levels. A hypocaloric or calorie free diet (e.g., STS) or a fasting mimicking diet (FMD) is administered for a first time period to the subject to reduce elevated triglycerides and/or CRP and/or other inflammatory markers levels. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In another refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, STS or a FMD can be repeated at intervals from one week to 6 months. In a refinement, the STS or a FMD can be repeated at intervals from one week to 2 months. Typically, the subject is administered a normal diet in between these repetitions.

In another embodiment, a method for elevated cholesterol and/or elevated LDL levels without lowering HDL levels in a subject is provided. The method includes a step of identifying a subject having elevated cholesterol and/or elevated LDL levels. A hypocaloric or calorie free diet (e.g., STS) or a fasting mimicking diet (FMD) is administered for a first time period to the subject to reduce elevated cholesterol and/or elevated LDL levels. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In a refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, a hypocaloric or calorie free diet or a FMD can be repeated at intervals from one week to 6 months. Typically, the subject is administered a normal diet in between these repetitions.

In still another embodiment, a method for reducing elevated insulin and/or glucose levels in a subject with elevated levels but not in subjects with low levels of glucose and insulin is provided. The method includes a step of identifying a subject having elevated insulin and/or glucose levels. A hypocaloric or calorie free diet (e.g., STS) or a fasting mimicking diet (FMD) is administered for a first time period to the subject to reduce elevated glucose and/or elevated insulin levels. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In a refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, a hypocaloric or calorie free diet can be repeated at intervals from one week to 6 months. In a refinement, the STS or a FMD can be repeated at intervals from one week to 2 months. Typically, the subject is administered a normal diet in between these repetitions.

In still another embodiment, a method for promoting chronic reduction of IGF-1 in a subject with elevated levels but not in subjects with low levels is provided. The method includes a step of identifying a subject having elevated IGF-1 levels. A hypocaloric or calorie free diet (e.g., STS) or a fasting mimicking diet (FMD) is administered for a first time period to the subject to reduce elevated IGF-1 levels. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In a refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, the hypocaloric or calorie free diet can be repeated at intervals from one week to 6 months. In a refinement, the STS or a FMD can be repeated at intervals from one week to 2 months. Typically, the subject is administered a normal diet in between these repetitions.

In still another embodiment, a method for treating a subject with elevated IGF-1 levels and promoting long-term lowering of IGF-1 levels without further lowering IGF-1 in subjects with already low levels is provided. The method includes a step of identifying a subject having elevated IGF-1 levels. A protein free normocaloric diet to the subject while providing the subject with a rice protein dietary supplement is administered for a first time period to the subject to reduce elevated IGF-1 levels. In a refinement, the protein free normocaloric diet is repeated a plurality of times at predetermined intervals. In a further refinement, the protein free normocaloric diet is administered for a period of 5 days every 2-24 weeks or 1-2 days every week. For example, protein free normocaloric diet can be repeated at intervals from one week to 6 months. In a refinement, the protein free normocaloric diet can be repeated at intervals from one week to 2 months. In another refinement the protein free diet in combination with the rice protein dietary supplement is used to replace any major meal or snack.

In another embodiment, the rice protein supplement is applied to patients on an FMD diet to reduce further any potential malnourishment while achieving all of the effects of the FMD on aging, and age-related diseases or its risk factors/markers. Typically, the subject is administered a normal diet in between these repetitions.

In still another embodiment, a method for method for reducing fatty liver is provided. The method includes a step of identifying a subject having elevated hepatic fat fraction. A hypocaloric or calorie free diet or a fasting mimicking diet (FMD) is administered for a first time period to the subject to reduce elevated IGF-1 levels. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In another refinement, the hypocaloric or calorie free diet or a fasting mimicking diet is repeated a plurality of times at predetermined intervals. In a further refinement, hypocaloric or calorie free diet or a fasting mimicking diet is administered for a period of 5 days every 2-24 weeks or 1-2 days every week. For example, the hypocaloric or calorie free diet or a fasting mimicking diet can be repeated at intervals from one week to 6 months. In a refinement, the hypocaloric or calorie free diet or a fasting mimicking diet can be repeated at intervals from one week to 2 months. Typically, the subject is administered a normal diet in between these repetitions.

In still another embodiment, a method for treating obesity and particularly abdominal/visceral fat in a subject is provided. The method includes a step of identifying a subject that is overweight. A hypocaloric or calorie free diet (e.g., STS) or a fasting mimicking diet (FMD) is administered for a first time period to the subject to specifically reduce the subject's fat mass without affecting the lean body mass. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In another refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, a hypocaloric or calorie free diet can be repeated at intervals from one week to 6 months. In a refinement, the hypocaloric or calorie free diet can be repeated at intervals from one week to 2 months. Typically, the subject is administered a normal diet in between these repetitions.

In still another embodiment, a method for extending life span and healthspan in a subject is provided. The method includes a step of administering a hypocaloric or calorie free diet (e.g., STS) or a fasting mimicking diet (FMD) for a first time period to the subject to reduce the subject's weight. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In another refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, a hypocaloric or calorie free diet can be repeated at intervals from one week to 6 months. In a refinement, the hypocaloric or calorie free diet can be repeated at intervals from one week to 2 months. Typically, the subject is administered a normal diet in between these repetitions.

In still another embodiment, a method for treating or preventing inflammation of inflammatory diseases is provided. In this embodiment, blood cortisol is increased thereby activating anti-inflammatory pathways. In a variation, a subject having an inflammatory disease or in need of having inflammation prevented is identified. A hypocaloric or calorie free diet (e.g., STS) or a fasting mimicking diet (FMD) is administered for a first time period to the subject to reduce the subject's weight. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In another refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, a hypocaloric or calorie free diet can be repeated at intervals from one week to 6 months. In a refinement, the hypocaloric or calorie free diet can be repeated at intervals from one week to 2 months. Typically, the subject is administered a normal diet in between these repetitions.

In yet another embodiment, a method for increasing regeneration is provided. In this embodiment, levels of stem or embryonic like stem cells including circulating mesenchymal stem/progenitor cells (MSPC) are increased. In a variation, a subject in need of regeneration is identified. A hypocaloric or calorie free diet (e.g., STS) or a fasting mimicking diet (FMD) is administered for a first time period to the subject to reduce the subject's weight. In general, the FMD diet provides less than about 1200 kilocalories per day when administered. In a refinement, the FMD diet provides less than, in increasing order of preference, 1200 kcal, 1100 kcal, 1000 kcal, 900 kcal, 700 kcal or 600 kcal per day when administered. In a further refinement, the FMD diet provides greater than, in increasing order of preference, 200 kcal, 250 kcal, 300 kcal, 350 kcal, 400 kcal or 500 kcal per day when administered. In another refinement, a hypocaloric or calorie free diet or a FMD is repeated a plurality of times at predetermined intervals. In a further refinement, the hypocaloric or calorie free diet or fasting mimicking diet is administered for a period of 5 days every 2-24 weeks or 1-2 days every week. For example, a hypocaloric or calorie free diet can be repeated at intervals from one week to 6 months. In a refinement, the hypocaloric or calorie free diet can be repeated at intervals from one week to 2 months. Typically, the subject is administered a normal diet in between these repetitions.

In each of the embodiments set forth herein, treatment of the subject can be extended over a period of years. For example, cycles of the hypocaloric or calorie free diet or a fasting mimicking diet (FMD) can be administered for 1 to 5 or more years. It should be appreciated that a normal diet is provided between cycles of the hypocaloric or calorie free diet or a FMD.

Examples of hypocaloric fasting mimicking diet or calorie free diet protocols are found in U.S. patent application Ser. Nos. 12/430,058 and 13/488,590; the entire disclosures of which are hereby incorporated by reference. The hypocaloric diet contains dietary materials capable of providing nutrition to a human subject while providing no more than 813-957 kcal (e.g., no more than 700, 500, 300, or 100 kcal, or 0 kcal) total energy, and no more than 30-36 g (e.g., no more than 20, 10, or 5 g, or 0 g) protein. If carbohydrates are present in the dietary materials, no more than half of the energy is in the carbohydrates. In a refinement, the hypocaloric/calorie free diet/FMD diet may be administered to the subject for 2-10 consecutive days. In an alternative method the diet can be administered for only 1 day with a frequency of at least 1 day/week every week of the month.

In another variation, the hypocaloric or calorie free diet provides nutrition while providing no more than 11 kcal (e.g., no more than 8, 5, or 2 kcal, or 0 kcal) energy per kilogram body weight of the subject per day and no more than 0.4 g (e.g., 0.3, 0.2, or 0.1 g or 0 g) protein per kilogram body weight of the animal or human per day. If carbohydrates are present in the diet, no more than half of the energy is in the carbohydrates. In some embodiments, the diet is capable of providing no more than 800 kcal (e.g., 600, 400, or 200 kcal or 0 kcal) total energy per day. The diet may be administered to animals or humans for 3-10 consecutive days. In an alternative method the diet can be administered for only 1 day with a frequency of at least 1 day/week every week of the month.

As set forth above, a subject is administered a normal diet i.e., re-feeding period) in between repetitions of the FMD for each of the variations and embodiments of the invention. In this context, a normal diet is a diet of sufficient caloric intake to maintain the patient weight. In a refinement, the normal caloric intake provides the subject with 1500 to 2500 kcal or 1800 to 2300 kcal, or 1800 to 2000 kcal.

Examples of FMD diets are found in U.S. patent application Ser. Nos. 14/060,494 and 14/178,953 and WIPO Pub. No. WO2011/050302 and WIPO Pub. No. WO2011/050302; the entire disclosures of which are hereby incorporated by reference. Typically, in the FMD protocol a subject's diet is substituted for a predetermined number of days (i.e. 5 days). During this period, subjects consume plenty of water. For healthy subjects of normal weight (Body Mass Index or BMI between 18.5-25), the diet is consumed once a month (5 days on the diet and 25-26 days on their normal diet) for the first 3 months and every 3 months thereafter (5 days every 3 months). The weight of the subject is measured and the subject must regain at least 95% of the weight lost during the diet before the next cycle is begun unless weight loss is advised by a physician or healthcare professional. Subjects with BMI of less than 18.5 should not undertake the FMD unless recommended and supervised by a physician. The same regimen (once every month for 3 months followed by once every 3 months thereafter) can be adopted for the treatment, or in support of the treatment, of all of the conditions presented in the patent applications. U.S. patent application Ser. No. 14/178,953 provides a low protein version of the FMD diet. In an alternative method the diet can be administered for only 1 day with a frequency of at least 1 day/week every week of the month.

In one variation, the FMD set forth in U.S. patent application Ser. No. 12/430,058 is used in the methods set forth above. This diet includes nutrition facts relative to calories, macronutrients and micronutrients. Calories are consumed according to the user's body weight. Total calorie consumption is 4.5-7 kcal per pound (or 10-16 kcal per kilogram) for day 1 and 3-5 kcal per pound (or 7-11 kcal per kilogram) for day 2 to 5. FIGS. 12-14 provides listings of the nutrients for day one through day five. In addition to the macronutrients, the diet should contain less than 30 g of sugar on day 1 and less than 20 g of sugar on days 2-5. The diet should contain less than 28 g of proteins on day 1 and less than 18 g of proteins on days 2-5. The diet should contain between 20 and 30 grams of monounsaturated fats on day 1 and 10-15 grams of monounsaturated fats on days 2-5. The diet should contain between 6 and 10 grams of polyunsaturated fats on day 1 and 3-5 grams of polyunsaturated fats on days 2-5. The diet should contain less than 12 g of saturated fats on day 1 and less than 6 grams of saturated fats on days 2-5. Typically, the fats on all days are derived from a combination of the following: Almonds, Macadamia Nuts, Pecans, Coconut, Coconut oil, Olive Oil and Flaxseed. In a refinement, the FMD diet includes over 50% of the recommended daily value of dietary fiber on all days. In the further refinement, the amount of dietary fiber is greater than 15 grams per day on all five days. The diet can contain 12-25 grams of glycerol per day on days 2-5. In a refinement, glycerol is provided at 0.1 grams per pound body weight/day.

In a refinement, the FMD includes the following micronutrients (at least 95% non-animal based): over 5,000 IU of vitamin A per day (days 1-5); 60-240 mg of vitamin C per day (days 1-5); 400-800 mg of Calcium per day (days 1-5); 7.2-14.4 mg of Iron per day (days 1-5); 200-400 mg of Magnesium per day (days 1-5); 1-2 mg of copper per day (days 1-5); 1-2 mg of Manganese per day (days 1-5); 3.5-7 mcg of Selenium per day (days 1-5); 2-4 mg of Vitamin B1 per day (days 1-5); 2-4 mg of Vitamin B2 per day (days 1-5); 20-30 mg of Vitamin B3 per day (days 1-5); 1-1.5 mg of Vitamin B5 per day (days 1-5); 2-4 mg of Vitamin B6 per day (days 1-5); 240-480 mcg of Vitamin B9 per day (days 1-5); 600-1000 IU of Vitamin D per day (days 1-5); 14-30 mg of Vitamin E per day (days 1-5); over 80 mcg of Vitamin K per day (days 1-5); 16-25 mcg Vitamin B12 are provided during the entire 5-day period; 600 mg of Docosahexaenoic acid (DHA, algae-derived) are provided during the entire 5-day period. The FMD diet provides high micronutrient content mostly (i.e., greater than 50 percent by weight) from natural sources including: Kale, Cashews, Yellow Bell Pepper, Onion, Lemon Juice, Yeast, Turmeric. Mushroom, Carrot, Olive Oil, Beet Juice, Spinach, Tomato, Collard, Nettle, Thyme, Salt, Pepper, Vitamin B12 (Cyanobalamin), Beets, Butternut Squash, Collard, Tomato, Oregano, Tomato Juice, Orange Juice, Celery, Romaine Lettuce, Spinach, Cumin, Orange Rind, Citric Acid, Nutmeg, Cloves, and combinations thereof. Table 1 provides an example of additional micronutrient supplementation that can be provided in the FMD diet:

TABLE 1

Micronutrient Supplementation

| | Supplement | Formula | Amount | Amount Range | Unit |
|---|---|---|---|---|---|
| Vit A | | | 1250 IU | 900-1600 | IU |
| Vit C | Ascorbic Acid | $C_6H_8O_6$ | 15.0000 | 10-20 | mg |
| Ca | Calcium Carbonate | $CaCO_3$ | 80.0000 | 60-100 | mg |
| Fe | Ferrous Fumarate | $C_4H_2FeO_4$ | 4.5000 | 3-6 | mg |
| Vit D3 | Cholecalciferol | $C_{27}H_{44}O$ | 0.0025 | 0.001-0.005 | mg |
| Vit E | dl-Alpha Tocopheryl Acetate | $C_{29}H_{50}O_2$ | 5.0000 | 3-7 | mg |
| Vit K | Phytonadione | | 0.0200 | 0.1-0.04 | mg |
| Vit B1 | Thiamine Mononitrate | $C_{12}H_{17}N_5O_4S$ | 0.3750 | 0.15-0.5 | mg |
| Vit B2 | Riboflavin E101 | $C_{17}H_{20}N_4O_6$ | 0.4250 | 0.2-0.6 | mg |
| Vit B3 | Niacinamide | $C_6H_6N_2O$ | 5.0000 | 3-7 | mg |

TABLE 1-continued

Micronutrient Supplementation

| | Supplement | Formula | Amount | Amount Range | Unit |
|---|---|---|---|---|---|
| Vit B5 | Calcium Pantothenate | $C_{18}H_{32}CaN_2O_{10}$ | 2.5000 | 1.5-4.0 | mg |
| Vit B6 | Pyridoxine Hydrochloride | $C_8H_{11}NO_3 \cdot HCl$ | 0.5000 | 0.3-0.7 | mg |
| Vit B7 | Biotin | $C_{10}H_{16}N_2O_3S$ | 0.0150 | 0.01-0.02 | mg |
| Vit B9 | Folic Acid | $C_{19}H_{19}N_7O_6$ | 0.1000 | 0.07-0.14 | mg |
| Vit B12 | Cyanocobalamin | $C_{63}H_{88}CoN_{14}O_{14}P$ | 0.0015 | 0.001-0.002 | mg |
| Cr | Chromium Picolinate | $Cr(C_6H_4NO_2)_3$ | 0.0174 | 0.014-0.022 | mg |
| Cu | Cupric Sulfate | $CuSO_4$ | 0.2500 | 0.18-0.32 | mg |
| I | Potassium Iodide | KI | 0.0375 | 0.03-0.045 | mg |
| Mg | Magnesium Oxide | MgO | 26.0000 | 20-32 | mg |
| Mn | Manganese Sulfate | $MnSO_4$ | 0.5000 | 0.3-0.7 | mg |
| Mo | Sodium Molybdate | $Na_2MoO_4$ | 0.0188 | 0.014-0.023 | mg |
| Se | Sodium Selenate | $Na_2O_4Se$ | 0.0175 | 0.014-0.023 | mg |
| Zn | Zinc Oxide | ZnO | 3.7500 | 3-5 | mg |

In another embodiment, a diet package for implemented the method forth above is provided. The diet package includes a first set of rations for a first diet to be administered for a first time period to a subject, the first diet providing from 4.5 to 7 kilocalories per pound of subject for a first day and 3 to 5 kilocalories per pound of subject per day for a second to fifth day of the first diet. The diet package includes rations that provide less than 30 g of sugar on the first day; less than 20 g of sugar on the second to fifth days; less than 28 g of proteins on the first day; less than 18 g of proteins on the second to fifth days; 20 to 30 grams of monounsaturated fats on the first day; 10 to 15 grams of monounsaturated fats on the second to fifth days; between 6 and 10 grams of polyunsaturated fats on the first day; 3 to 5 grams of polyunsaturated fats on the second to fifth days; less than 12 g of saturated fats on the first day; less than 6 grams of saturated fats on the second to fifth days; and 12 to 25 grams of glycerol per day on the second to fifth days. In a refinement, the diet package further includes sufficient rations to provide the micronutrients set forth above. In a further refinement, the diet package provides instructions providing details of the methods set forth above.

In refinement of the embodiments set forth above, a 5-day supply of diet includes: soups/broths, soft drinks, nut bars and supplements. The diet is administered as follows: 1) on the first day a 1000-1200 kcal diet with high micronutrient nourishment as set forth above is provided; 2) for the next 4 days a daily diet of 650-800 kcal plus a drink containing a glucose substitution carbon source providing between 60-120 kcal are provided.

In another refinement of the embodiments set forth above, a 6-day low-protein diet protocol includes: soups/broths, soft drinks, nut bars, and supplements. The diet is administered as follows: 1) on the first day a 1000-1200 kcal diet plus with high micronutrient nourishment is provided; 2) for the next 3 days a daily diet of less than 200 kcal plus a drink containing a glucose substitution carbon source providing between 60 and 120 kcal. This substitution carbon source does not interfere with the effect of fasting on stem cell activation; 3) on the 5th day the subject consumes a normal diet; and 4) on day 6 additional replenishment foods consisting of a high fat source of 300 kcal and a micronutrient nourishment mix are provided in addition to normal diet.

In still another refinement, a diet protocol includes: 6-day supply of low-protein diet includes: soups/broths, soft drinks, nut bars, and supplements. 1) on the first day a 1000-1200 kcal diet with high micronutrient nourishment is provided; 2) for the next 3 days a daily diet of 600 to 800 kcal which contains less than 10 grams of protein and less than 200 kcal from sugars; 3) on the 5th day the subject receives a normal diet; and 4) on day 6 additional replenishment foods consisting of a high fat source of 300 kcal and a micronutrient nourishment mix are provided in addition to normal diet.

Although the FMD diet encompasses virtually any source of fat, sources high in unsaturated fat, including monounsaturated and polyunsaturated fat sources, are particularly useful (e.g., omega-3/6 essential fatty acids). Suitable examples of monounsaturated food sources include, but are not limited to, peanut butter, olives, nuts (e.g., almonds, pecans, pistachios, cashews), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The first diet also includes a component selected from the group consisting of vegetable extracts, minerals, omega-3/6 essential fatty acids, and combinations thereof. In one refinement, such a vegetable extract provides the equivalent of 5 recommended daily servings of vegetables. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish such as salmon, tuna, mackerel, bluefish, swordfish, and the like.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

The following FMDs and FMD regimens effectively manage body weight, risk factors associated with aging and age-related diseases in humans. They were developed based on animal studies as well as based on the results of ongoing clinical trials. It is shown that cycles of the FMD decrease fasting blood glucose and IGF-1 levels. The reduction of serum IGF-1 level may be responsible for the regeneration of stem and progenitor cells. The FMD regimens do not require chronic reduction of calorie intake, nor changes in the diet in between cycles, nor do they cause chronic weight loss.

The FMD is comprised of a variety of food items including, but not limited to, energy bars, soups, vegetable chips, vegetable and fruit snacks, energy drinks, supplements for minerals, vitamins and essential fatty acids. All food items were developed to reach a profile of macronutrients and calorie content that will mimic the benefit of short-term starvation while providing certain levels of support for micronutrients. In some variations, FMDs are formulated with rice-derived protein at low to moderate protein levels (5%-10% total calorie derived from protein) as a method to reduce IGF-1 levels (see FIGS. 3-6) and maximize fasting mimicking effects.

Diet 1: the FMD will substitute a subject's normal diet for a period of 5 days every 2-12 weeks depending on the need of the subject in terms of body weight and disease risk factor management. For day 1, the FMD will provide 4.5-7 kcal per pound of body weight (or 10-16 kcal per kilogram body weight). For days 2-5, the FMD will provide 3-5 kcal per pound of body weight (or 7-11 kcal per kilogram body weight). The day 1 diet should contain less than 30 grams of sugar, less than 28 grams of protein, 20-30 grams of monounsaturated fats, 6-10 grams of polyunsaturated fats and 2-12 grams of saturated fats. The Day 2-5 diets should contain less than 20 grams of sugar, less than 18 grams of protein, 10-15 grams of monounsaturated fats, 3-5 grams of polyunsaturated fats and 1-6 grams of saturated fats. The diet will also provide micronutrients at greater than 25% of the Daily Value (DV). In an alternative method the diet can be administered for only 1 day with a frequency of at least 1 day/week every week of the month. Proteins can be of any source but plant based proteins and particularly rice-derived can enhance the fasting mimicking effects.

Diet 2: the FMD will substitute a subject's normal diet for a period of 2 days every week. The FMD will provide 3-5 kcal per pound of body weight (or 7-11 kcal per kilogram body weight). The day 1 diet should contain less than 30 grams of sugar, less than 28 grams of protein, 20-30 grams of monounsaturated fats, 6-10 grams of polyunsaturated fats and 2-12 grams of saturated fats. The day 2 diet should contain less than 20 grams of sugar, less than 18 grams of protein, 10-15 grams of monounsaturated fats, 3-5 grams of polyunsaturated fats and 1-6 grams of saturated fats. The diet will also provide micronutrients at greater than 25% of the Daily Value (DV).

FIG. 1. Starting at 17-month of age, female C57BL/6 mice were subjected to cycles of 5-day FMD every 2 weeks. A) Mice fed with FMD regained body weight upon refeeding. FMD is not associated with chronic body weight loss. B) Cycles of FMD initiated at middle age (17 month old) extended mean lifespan. FMD reduced blood glucose (C), IGF-1 (D) and insulin (E), all of which recovered after refeeding of normal diet. FMD increased white blood cell (WBC) (F) and lymphocyte (LYM) (G) counts.

Figure 2A:
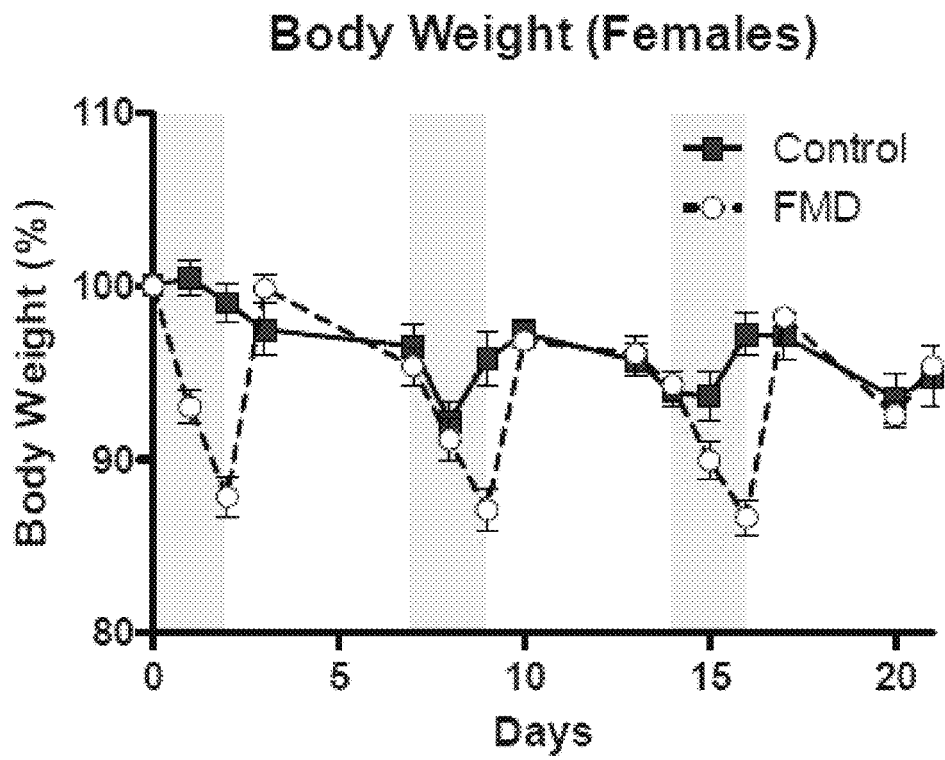
FIGS. 2A and 2B. 18-month old female C57BL/6 mice were subjected to cycles of 2-day FMD every week. A) Body weight recovered quickly after refeeding of normal diet. B) FMD reduced blood glucose.
Figure 2B:
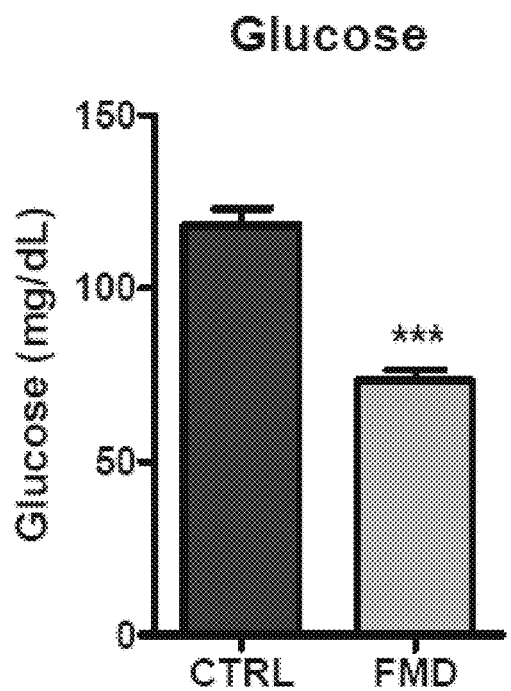
Figure 3A:
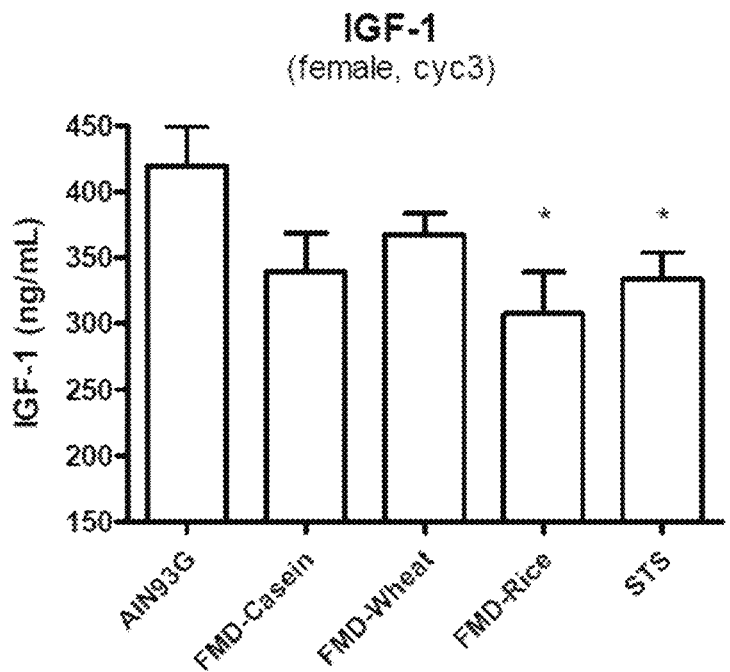
FIGS. 3A, 3B, 3C, 3D, 3E, 3F, and 3G. 18-month old female (A) and male (B) C57BL/6 mice were subjected to 3 cycles or 1 cycle of a rice protein-based fasting mimicking and enhancing diet (FMED-R) for 5 days every two weeks. Rice protein-based FMD with moderate and low protein content (R-M and R-L) significantly lowered circulating IGF-1, comparable to short-term starvation (STS). 18-months old male (B) C57BL/6 mice were fed with rice-protein based FMDs with low or moderate levels of protein (R-M and R-L, respectively): C) Body weight recovered quickly after refeeding of normal diet. FMDs reduced blood glucose (D), and increased ketone bodies (E). As during short-term starvation, FMD feeding led to a drop in white blood cell (WBC) and lymphocyte counts (G), which recovers after a week of refeeding of normal diet.
Figure 3B:
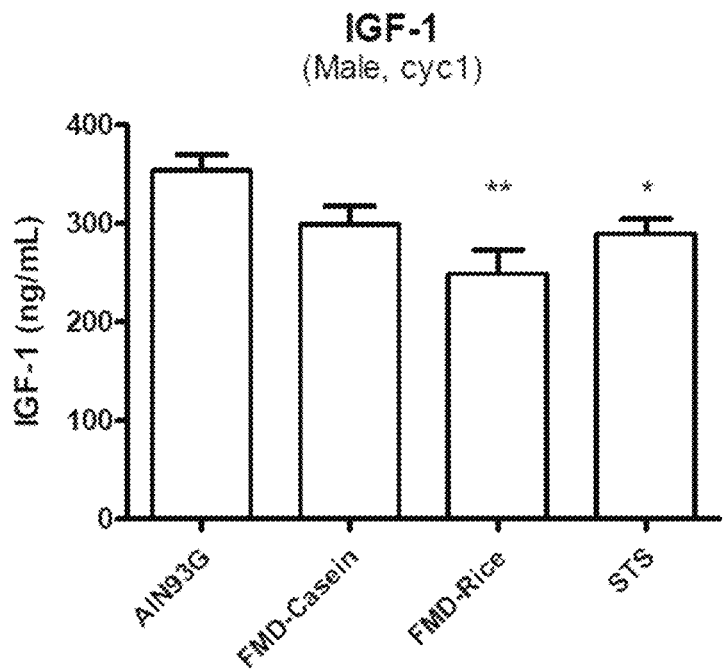
Figure 3C:
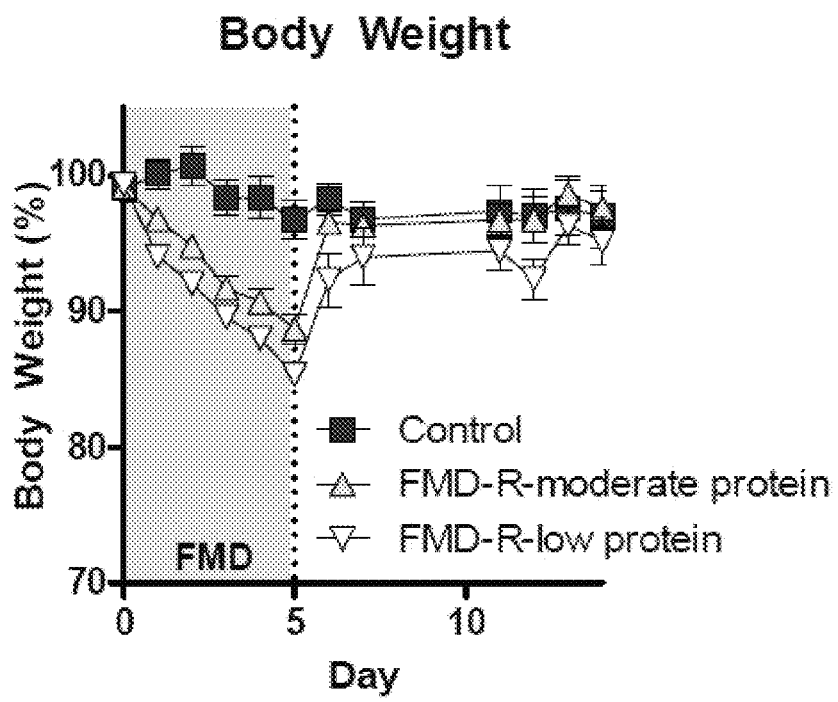
Figure 3D:
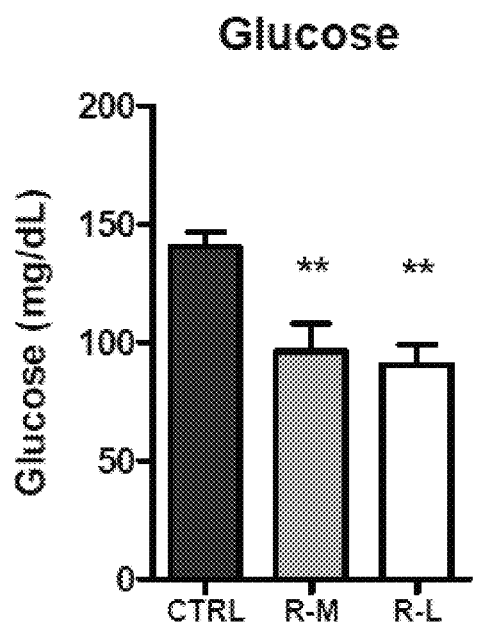
Figure 3E:
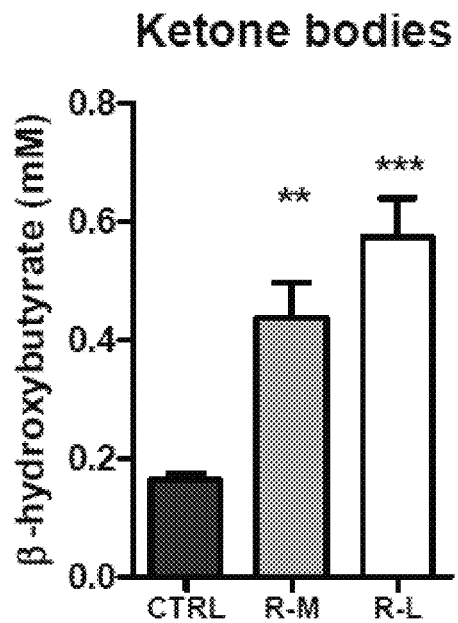
Figure 3F:
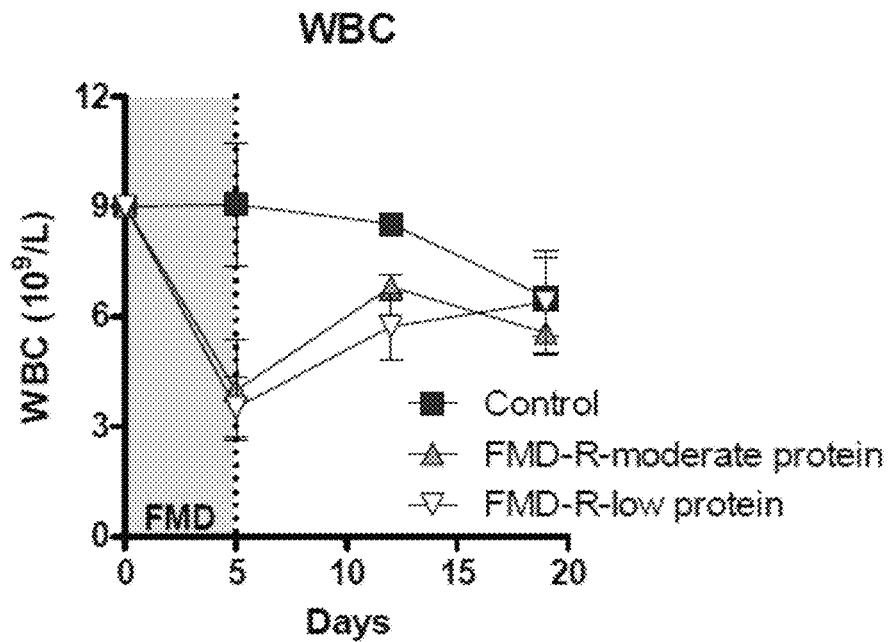
Figure 3G:
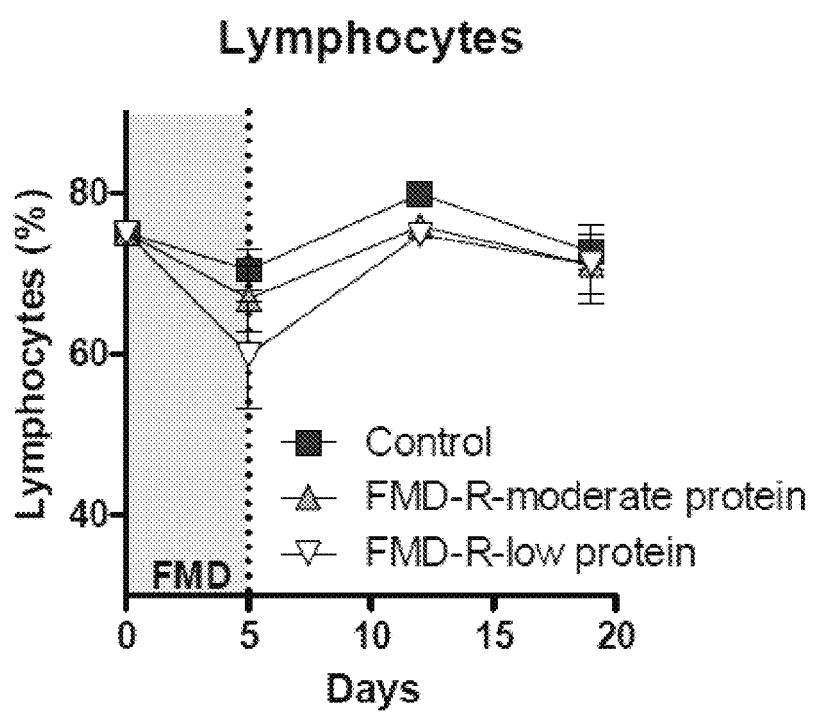
Figure 4A:
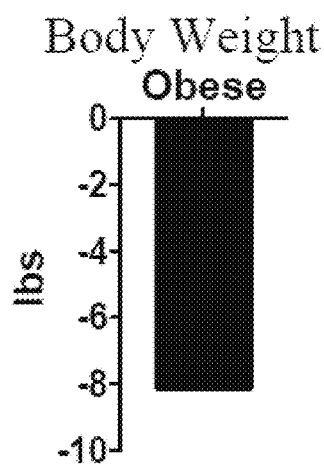
Figure 4B:
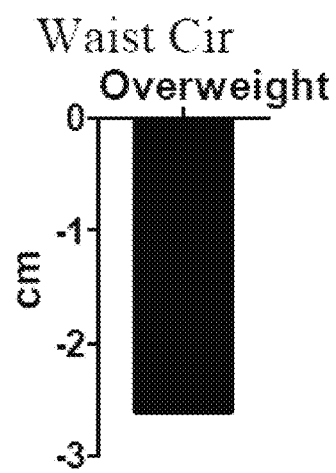
Figure 4C:
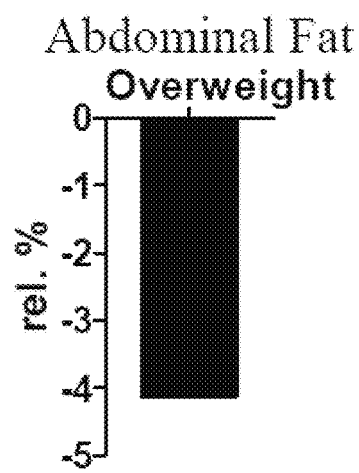
Figure 4D:
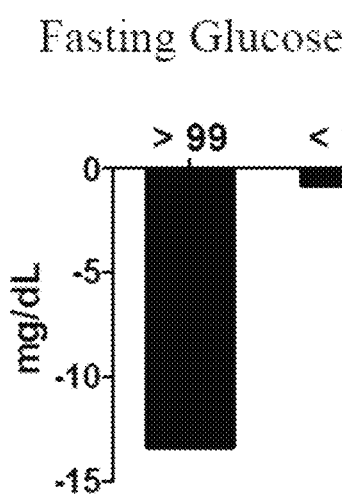
Figure 4E:
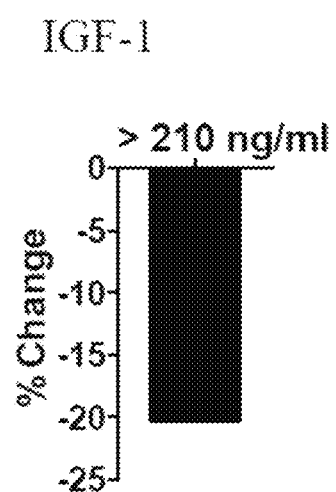
Figure 4I:
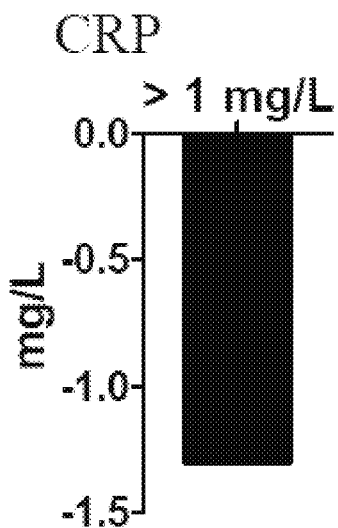
Figure 4J:
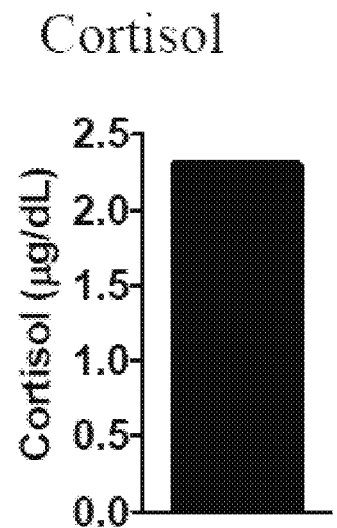
Figure 4K:
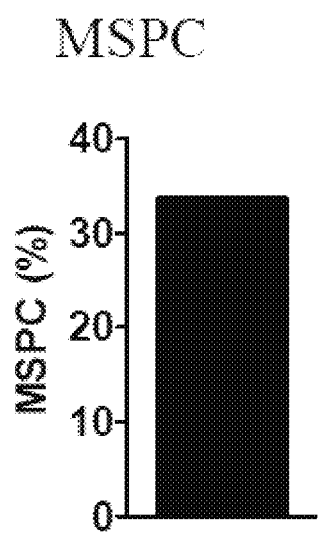

FIG. 2. 18-month old female C57BL/6 mice were subjected to cycles of 2-day FMD every week. A) Body weight recovered quickly after refeeding of normal diet. B) FMD reduced blood glucose.

FIG. 3. 18-month old female (A) and male (B) C57BL/6 mice were subjected to 3 cycles or 1 cycle of a rice protein-based fasting mimicking and enhancing diet (FMED-R) for 5 days every two weeks. Rice protein-based FMD with moderate and low protein content (R-M and R-L) significantly lowered circulating IGF-1, comparable to short-term starvation (STS). 18-months old male (B) C57BL/6 mice were fed with rice-protein based FMDs with low or moderate levels of protein (R-M and R-L, respectively): C) Body weight recovered quickly after refeeding of normal diet. FMDs reduced blood glucose (D), and increased ketone bodies (E). As during short-term starvation, FMD feeding led to a drop in white blood cell (WBC) and lymphocyte counts, which recovers after a week of refeeding of normal diet.

FIG. 4. Generally healthy participants were subjected to 3 cycles of a fasting mimicking diet (FMD) in three months. FMD reduced the body weight (A), waist circumference (B), and abdominal fat (C) in obese (BMI>30) and overweight (BMI>25) people. FMD reduced fasting blood sugar in people with prediabetes (fasting glucose >99 mg/dL). FMD reduced circulating IGF-1 levels (E). FMD reduced both systolic and diastolic blood pressure in people with above normal blood pressure (>120/80 mmHg). FMD reduced total cholesterol and LDL levels (G). FMD reduced triglycerides and CRP levels in people with relatively high levels of triglycerides (H) and CRP (I). FMD increased blood cortisol level (J) and circulating mesenchymal stem/progenitor cells (MSPC) (K).

Based on these results, FMD is an effective all natural plant-based dietary intervention to reduce abdominal adiposity and to reduce common biomarkers/risk factors for age-related diseases. In addition, it can promotes protective, anti-inflammatory, regenerative, and rejuvenating effects while providing high nourishment and allowing subjects to consume a relatively normal diet.

FMD Composition

Fasting Mimicking Diet (FMD) is all natural plant-based dietary intervention to manage body weight, to reduce circulating Insulin-like Growth Factor 1 (IGF-1) and to augment common markers/risk factors for age-related diseases. In addition, it may promote protective, anti-inflammatory, regenerative, and rejuvenating effects while providing high nourishment and allowing practitioners to enjoy a relatively normal diet.

The following FMD and FMD regimens will be required to effectively manage body weight, augment risk factors associated with aging and age-related diseases in humans. They were developed by extrapolating from the mouse diets and diet regimens as well as based on the results of ongoing clinical trials.

It has been shown that the FMD, intermittent use of FMD, and cycles of FMD decreases fasting blood glucose and IGF-1 levels. The reduction of serum IGF-1 level has been shown to be one of the key biomarkers that is associated with regeneration of the hematopoietic stem and progenitor cells (HSPCs).

The FMD is comprised of a variety of food items including, but not limited to, energy bars, soups, vegetable chips, vegetable and fruit snacks, energy drinks, teas, and supplements for minerals, vitamins and essential fatty acids. All food items were developed to reach a profile of macro nutrients and calorie content that will mimicking the benefit of short-term fasting while providing certain levels of support for micronutrients.

ProLon Diet

Diet 1: the FMD will substitute a subject's normal diet for a period of 5 days every 2-4 weeks depending on the need of the subject in terms of body weight and disease risk factor management. For day 1, the FMD will provide 4-8 kcal per pound of body weight (or 9-18 kcal per kilogram body weight). For day 2-5, the FMD will provide 3-6 kcal per pound of body weight (or 6-13 kcal per kilogram body weight). The day 1 diet should contain less than 40 grams of sugar, less than 28 grams of protein, 12-25 grams of monounsaturated fats, 4.5-10 grams of polyunsaturated fats and 4.5-10 grams of saturated fats. The Day 2-5 diets should contain less than 25 grams of sugar, less than 18 grams of protein, 9-18 grams of monounsaturated fats, 3-6 grams of polyunsaturated fats and 4-8 grams of saturated fats. The diet will also provide micronutrients at greater than 50% of the Daily Value.

Rice-Protein Based Mix to Reduce IGF-1 Levels

We have identified a formulation that can replace other common protein sources to reduce circulating IGF-1 levels. The mix is composed of vitamins, minerals, essential fatty acids and enzymatically processed rice protein from whole grain, sprouted brown rice. This supplement mix will provide 17-35 gram of protein per day and micronutrients at greater than 25% of the Daily Value (DV).

Figure 5:
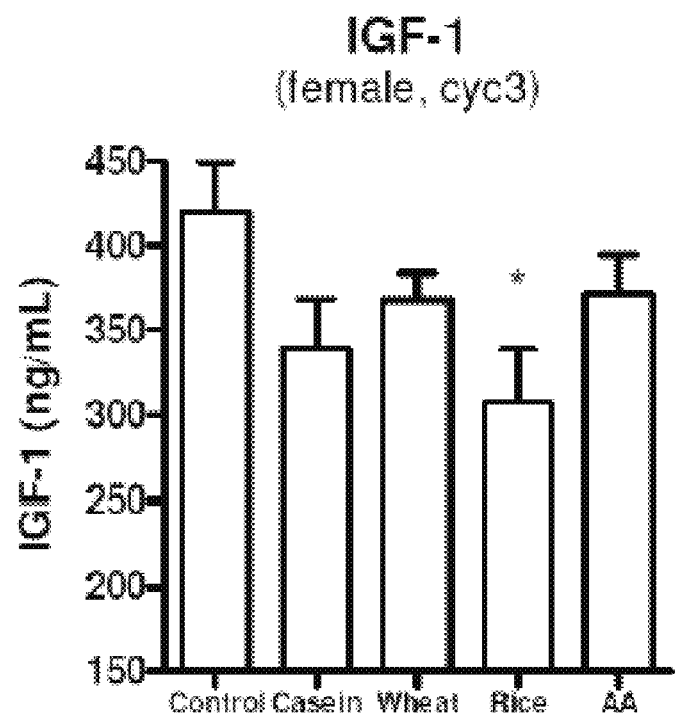
FIG. 5 provides serum IGF-1 levels in 18-month old female mice after 3 cycles of 5-days feeding of Control (AIN93G) or FMDs formulated with equivalent levels of casein-derived, wheat-derived, whole grain sprouted brown rice-derived proteins or an equivalent level of a complete amino acid mix as a protein source. (N=5). * $p<0.01$, ANOVA, compared to AIN93G.

FIG. 5 provides serum IGF-1 levels in 18-month old female mice after 3 cycles of 5-days feeding of Control (AIN93G) or FMDs formulated with equivalent levels of casein-derived, wheat-derived, whole grain sprouted brown rice-derived proteins or an equivalent level of a complete amino acid mix as a protein source. (N=5). * $p<0.01$, ANOVA, compared to AIN93G.

Figure 6:
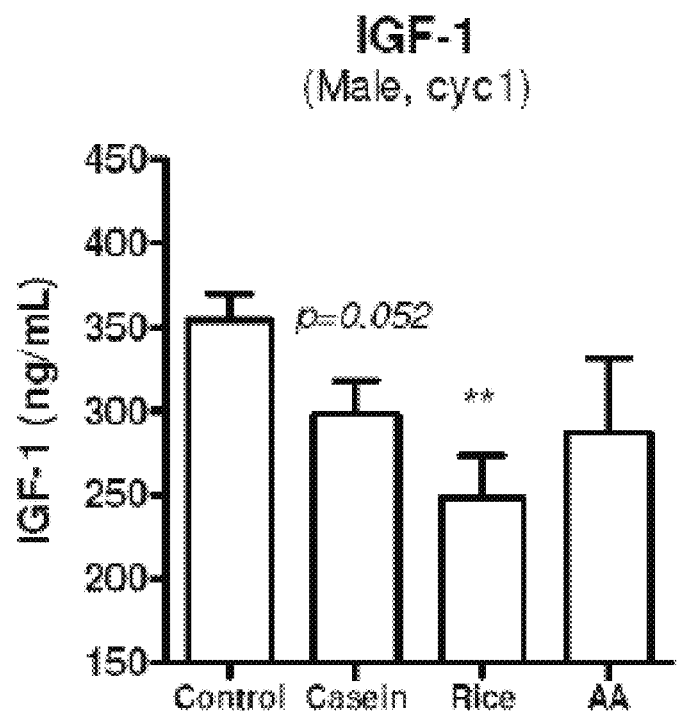
FIG. 6 provides serum IGF-1 levels of 18-month old male mice after 5-days feeding of Control (AIN93G) or FMDs formulated with casein-derived, or whole grain sprouted brown rice-derived protein or complete amino acid mix as protein source. (N=5). * $p<0.01$, ANOVA, compared to AIN93G.
Figure 7C:
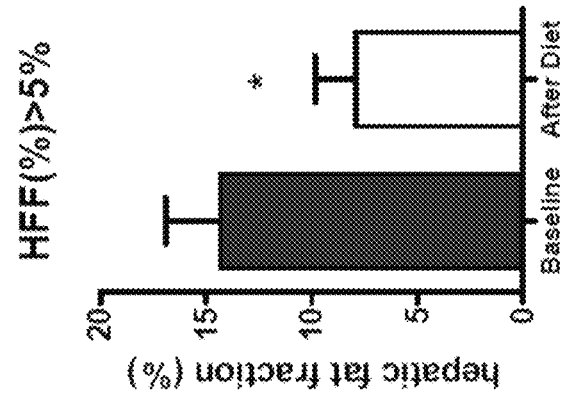
FIGS. 7A, 7B, and 7C. Generally healthy participants were subjected to 3 cycles of a fasting mimicking diet (FMD) in three months. Abdominal MRI study showed that (A) FMD reduced hepatic fat fraction (HFF) (N=15, $p<0.05$, paired t test, two-tailed). This effect is more pronounced in subjects that are (B) overweight (BMI>25, N=8, $p<0.05$, paired t test, two-tailed) and in those with (C) fatty liver (defined as baseline HFF>5%, N=5, $p<0.05$, paired t test, two-tailed).
Figure 7B:
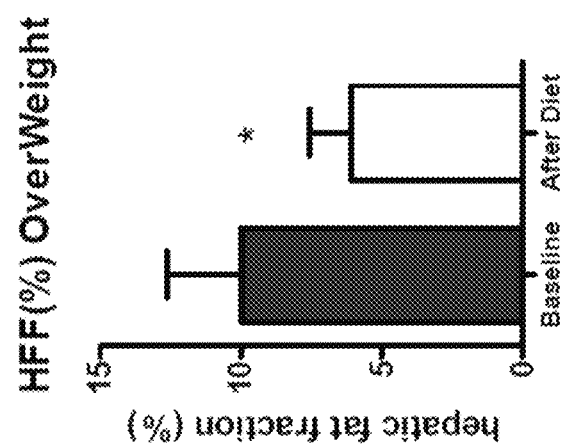
Figure 7A:
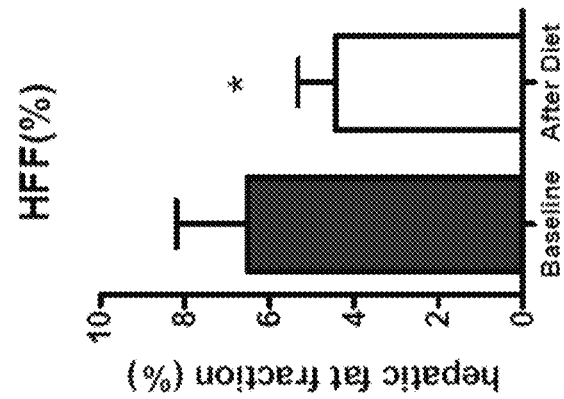

FIG. 6 provides serum IGF-1 levels of 18-month old male mice after 5-days feeding of Control (AIN93G) or FMDs formulated with casein-derived, or whole grain sprouted brown rice-derived protein or complete amino acid mix as protein source. (N=5). * $p<0.01$, ANOVA, compared to AIN93G.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for treating a subject with elevated insulin, the method comprising:
    a) identifying a subject having elevated insulin; and
    b) administering a hypocaloric or a fasting mimicking diet (FMD) to the subject to reduce elevated insulin, the hypocaloric or fasting mimicking diet providing less than 30 grams of sugar on day 1, less than 28 grams of protein on day 1, 20-30 grams of monounsaturated fats on day 1, 6-10 grams of polyunsaturated fats on day 1, 2-12 grams of saturated fats on day 1, less than 20 grams of sugar on days 2-5, less than 18 grams of protein on days 2-5, 10-15 grams of monounsaturated fats on days 2-5, 3-5 grams of polyunsaturated fats on days 2-5, and 1-6 grams of saturated fats on days 2-5 wherein a rice-protein based mix is provided as a source of protein, the rice-protein based mix being composed of vitamins, minerals, essential fatty acids and enzymatically processed rice protein from whole sprouted brown rice.

2. The method of claim 1 wherein the hypocaloric or fasting mimicking diet is administered for a period of 5 days every 2-12 weeks.

3. The method of claim 1 wherein step b) is repeated a plurality of times at predetermined intervals.

4. The method of claim 2 wherein step b) is repeated at intervals from one week to 6 months.

5. The method of claim 3 wherein the subject is administered a normal diet in between repetition of step b).

6. The method of claim 1 wherein the fasting mimicking diet is administered to the subject.

7. A method for treating a subject with elevated insulin, the method comprising:
    a) identifying a subject having elevated insulin; and
    b) administering a hypocaloric or fasting mimicking diet (FMD) to the subject to reduce elevated insulin levels, the hypocaloric or fasting mimicking diet providing less than 30 grams of sugar on day 1, less than 28 grams of protein on day 1, 20-30 grams of monounsaturated fats on day 1, 6-10 grams of polyunsaturated fats on day 1, 2-12 grams of saturated fats on day 1, less than 20 grams of sugar on day 2, less than 18 grams of protein on day 2, 10-15 grams of monounsaturated fats on day 2, 3-5 grams of polyunsaturated fats on day 2 and 1-6 grams of saturated fats on day 2;
    c) administering a normal diet on day 5; and
    d) administering replenishment foods consisting of a high fat source of 300 kcal and a micronutrient nourishment mix on day 6 in addition to the normal diet.

8. The method of claim 7 wherein the fasting mimicking diet is administered to the subject.

* * * * *